(12) United States Patent
Shin et al.

(10) Patent No.: US 8,951,194 B2
(45) Date of Patent: Feb. 10, 2015

(54) ULTRASOUND IMAGE PROCESSING BASED ON MOTION DEGREE OF ULTRASOUND PROBE

(75) Inventors: Dong Kuk Shin, Seoul (KR); Jong Sik Kim, Seoul (KR)

(73) Assignee: Samsung Medison Co., Ltd., Hongcheon-Gun, Gangwon-Do (KR)

( * ) Notice: Subject to any disclaimer, the term of this patent is extended or adjusted under 35 U.S.C. 154(b) by 633 days.

(21) Appl. No.: 12/951,729

(22) Filed: Nov. 22, 2010

(65) Prior Publication Data

US 2011/0125018 A1    May 26, 2011

(30) Foreign Application Priority Data

Nov. 25, 2009  (KR) .......................... 10-2009-0114280

(51) Int. Cl.
*A61B 8/00* (2006.01)
*A61B 8/08* (2006.01)

(52) U.S. Cl.
CPC ................. *A61B 8/08* (2013.01); *A61B 8/4254* (2013.01)
USPC ............ 600/437; 600/407; 600/443; 600/447

(58) Field of Classification Search
USPC .................................. 600/407, 437, 443, 447
See application file for complete search history.

(56) References Cited

U.S. PATENT DOCUMENTS

| | | | |
|---|---|---|---|
| 6,589,176 B2 * | 7/2003 | Jago et al. .................... | 600/443 |
| 7,575,551 B2 | 8/2009 | Watanabe et al. | |
| 8,162,835 B2 | 4/2012 | Ichikawa et al. | |
| 2006/0253024 A1 * | 11/2006 | Altmann et al. .............. | 600/437 |
| 2007/0265531 A1 * | 11/2007 | He et al. ......................... | 600/454 |
| 2008/0015435 A1 * | 1/2008 | Cribbs et al. ................... | 600/437 |
| 2008/0262354 A1 | 10/2008 | Yoshida et al. | |

FOREIGN PATENT DOCUMENTS

| | | |
|---|---|---|
| JP | 2005-000638 A | 1/2005 |
| JP | 2005-279013 A | 10/2005 |
| JP | 2005-312577 A | 11/2005 |
| JP | 2007-275457 A | 10/2007 |

(Continued)

OTHER PUBLICATIONS

Korean Office Action, issued in Korean Patent Application No. 10-2009-0114280, dated Dec. 28, 2011.

(Continued)

*Primary Examiner* — Joel Lamprecht
(74) *Attorney, Agent, or Firm* — McDermott Will & Emery LLP

(57) ABSTRACT

Embodiments for processing ultrasound images based on a motion degree of an ultrasound probe in an ultrasound system are disclosed. In one embodiment, the ultrasound system includes: an ultrasound acquisition unit including an ultrasound probe for transmitting ultrasound signals to a target object and receiving echo signals, the ultrasound acquisition unit being configured to form a plurality of ultrasound data based on the echo signals; and a processing unit coupled to the ultrasound acquisition unit and configured to form first to $N^{th}$ ultrasound images by using the plurality of ultrasound data, wherein N is a positive integer greater than 1, the processing unit being further configured to estimate a motion degree of an ultrasound probe and process the $N^{th}$ ultrasound image based on the motion degree.

15 Claims, 3 Drawing Sheets

(56) References Cited

FOREIGN PATENT DOCUMENTS

| | | | |
|---|---|---|---|
| JP | 2007-330764 A | 12/2007 | |
| JP | 2008-295859 A | 12/2008 | |
| JP | 2010-201049 A | 9/2010 | |
| KR | 10-2008-0060625 A | 7/2008 | |
| KR | 10-2009-0041475 A | 4/2009 | |
| WO | WO-2005/020821 A1 | 3/2005 | |
| WO | WO 2006/068103 | 6/2006 | |

OTHER PUBLICATIONS

Korean Notice of Allowance issued in Korean Patent Application No. 10-2009-0114280 dated Aug. 28, 2012.

Non-Final Rejection Japanese Patent Application No. 2010-262728 dated Apr. 30, 2014 with English translation.

* cited by examiner

ULTRASOUND IMAGE PROCESSING BASED ON MOTION DEGREE OF ULTRASOUND PROBE

CROSS-REFERENCE TO RELATED APPLICATIONS

The present application claims priority from Korean Patent Application No. 10-2009-0114280 filed on Nov. 25, 2009, the entire subject matter of which is incorporated herein by reference.

TECHNICAL FIELD

The present disclosure generally relates to ultrasound signal processing, and more particularly to ultrasound image processing based on a motion degree of an ultrasound probe in an ultrasound system.

BACKGROUND

Recently, an ultrasound system has been extensively used in the medical field due to its non-invasive and non-destructive nature. Modern high-performance ultrasound imaging diagnostic systems and techniques are commonly used to produce two- or three-dimensional ultrasound images of internal features of patients. To provide the ultrasound images, the ultrasound system operates in various image modes such as a brightness mode, a Doppler mode, an elastic image mode and the like to acquire ultrasound images for diagnosis.

Generally, the ultrasound system transmits ultrasound signals to a target object and receives echo signals to thereby form an ultrasound image. The transmission and reception of the ultrasound signals may be repeatedly carried out in a sequential manner so that a plurality of ultrasound images may be formed.

The ultrasound system may operate in various modes, e.g., a brightness mode, a Doppler mode, an elasticity mode, a 3-dimensional mode and the like. When the Doppler mode or the elasticity mode is selected, it is preferable that an ultrasound probe for transmission and reception of ultrasound signals is kept at an identical position on a target object to obtain better images in such modes. However, since the surface of a human body is curved and a user's hand may be moved, it may be difficult to keep the ultrasound probe at the fixed position. Thus, image qualities in such modes may be degraded due to the motion of the ultrasound image.

SUMMARY

Embodiments for processing an image based on a motion degree of an ultrasound probe in an ultrasound system are disclosed herein. In one embodiment, by way of non-limiting example, an ultrasound system includes: an ultrasound acquisition unit including an ultrasound probe for transmitting ultrasound signals to a target object and receiving echo signals, the ultrasound acquisition unit being configured to form a plurality of ultrasound data based on the echo signals; and a processing unit coupled to the ultrasound acquisition unit and being configured to form first to $N^{th}$ ultrasound images by using the plurality of ultrasound data, wherein N is a positive integer greater than 1, the processing unit being further configured to estimate a motion degree of an ultrasound probe and process the $N^{th}$ ultrasound image based on the motion degree.

In another embodiment, a method of estimating a motion degree of an ultrasound probe to process an ultrasound image in an ultrasound system, comprises: a) transmitting ultrasound signals to a target object and receiving echo signals to form a plurality of ultrasound data based on the echo signals; b) forming first to $N^{th}$ ultrasound images by using the plurality of ultrasound data, wherein N is a positive integer greater than 1; c) estimating a motion degree of an ultrasound probe by using the ultrasound images; and d) processing the $N^{th}$ ultrasound image based on the motion degree.

In yet another embodiment, a method of estimating a motion degree of an ultrasound probe to process an ultrasound image in an ultrasound system, comprises: a) transmitting ultrasound signals to a target object and receiving echo signals to form a plurality of ultrasound data based on the echo signals; b) forming first to $N^{th}$ ultrasound images by using the plurality of ultrasound data, wherein N is a positive integer greater than 1; c) sensing a position of the ultrasound probe to form a sensing signal; d) estimating a motion degree of an ultrasound probe based on the sensing signal; and e) processing the $N^{th}$ ultrasound image based on the motion degree.

The Summary is provided to introduce a selection of concepts in a simplified form that are further described below in the Detailed Description. This Summary is not intended to identify key or essential features of the claimed subject matter, nor is it intended to be used in determining the scope of the claimed subject matter.

DETAILED DESCRIPTION

A detailed description may be provided with reference to the accompanying drawings. One of ordinary skill in the art may realize that the following description is illustrative only and is not in any way limiting. Other embodiments of the present invention may readily suggest themselves to such skilled persons having the benefit of this disclosure.

Figure 1:
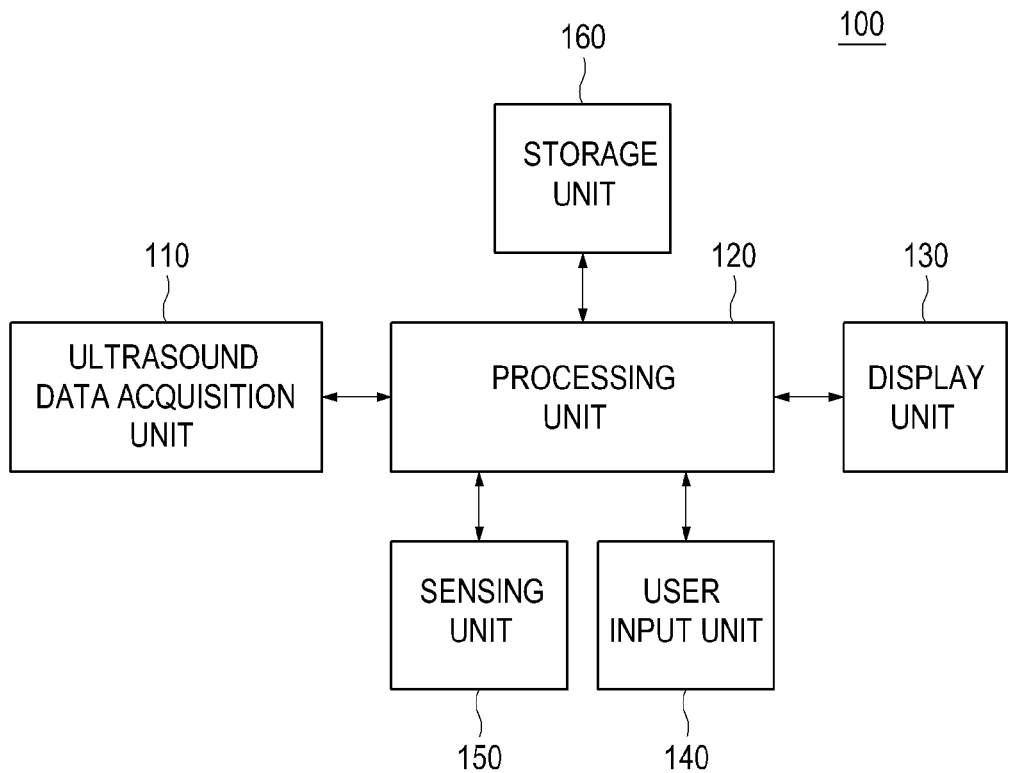
FIG. 1 is a block diagram showing an illustrative embodiment of an ultrasound system.

Referring to FIG. 1, an illustrative embodiment of an ultrasound system 100 is shown. As depicted therein, the ultrasound system 100 may include an ultrasound data acquisition unit 110, a processing unit 120 and a display unit 130. In one embodiment, the ultrasound system 100 may further include a user input unit 140, a sensing unit 150 and a storage unit 160.

Figure 2:
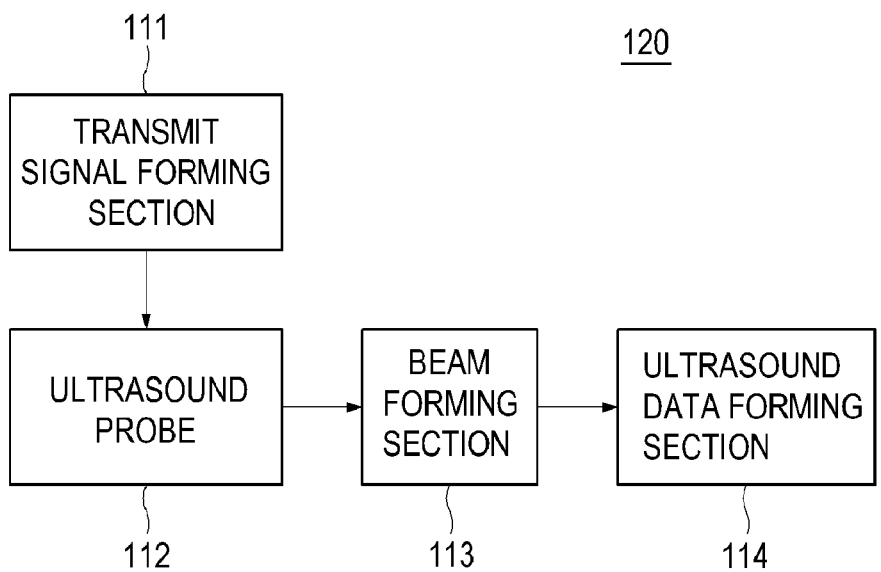
FIG. 2 is a block diagram showing an illustrative embodiment of an ultrasound data acquisition unit.

The ultrasound data acquisition unit 110 may be configured to transmit ultrasound signals to a target object and receive echo signals reflected from the target object to thereby acquire ultrasound data. As shown in FIG. 2, the ultrasound data acquisition unit 110 may include a transmit signal forming section 111. The transmit signal forming section 111 may be configured to form transmit signals according to image modes such as a brightness mode (B-mode), a Doppler mode (D-mode), a color Doppler mode (C-mode), an elasticity mode, a 3-dimensional mode and the like. The transmit signal forming section 111 may repeatedly form transmit signals in a sequential manner to thereby form a plurality of transmit signals.

The ultrasound data acquisition unit 110 may further include an ultrasound probe 112, which is coupled to the transmit signal forming section 111. The ultrasound probe 112 may include transducer elements that may be configured to output ultrasound signals, which may be propagated into the target object, in response to the transmit signals. The ultrasound probe 112 may receive echo signals reflected from the target object to thereby output receive signals. The ultrasound probe 112 may include a 3-dimensional mechanical probe, a 2-dimensional probe and the like.

The ultrasound data acquisition unit 110 may further include a beam forming section 113, which is coupled to the ultrasound probe 112. The beam forming section 113 may be configured to digitize the receive signals to thereby output digital signals. The beam forming section 113 may be further configured to apply delays to the digital signals in consideration of distances between the transducer elements and focal points, thereby forming a plurality of receive-focused signals.

The ultrasound data acquisition unit 110 may further include an ultrasound data forming section 114, which is coupled to the beam forming section 113. The ultrasound data forming section 114 may be configured to form a plurality of ultrasound data based on the receive-focused signals.

The processing unit 120, which is coupled to the ultrasound data acquisition unit 110, is configured to form a plurality of ultrasound images based on the plurality of ultrasound data. The processing unit 120 may be further configured to estimate a motion of the ultrasound probe 112 and process the ultrasound images based on the estimated motion. The operation of the processing unit 120 will be described in detail with reference to FIG. 3.

Figure 3:
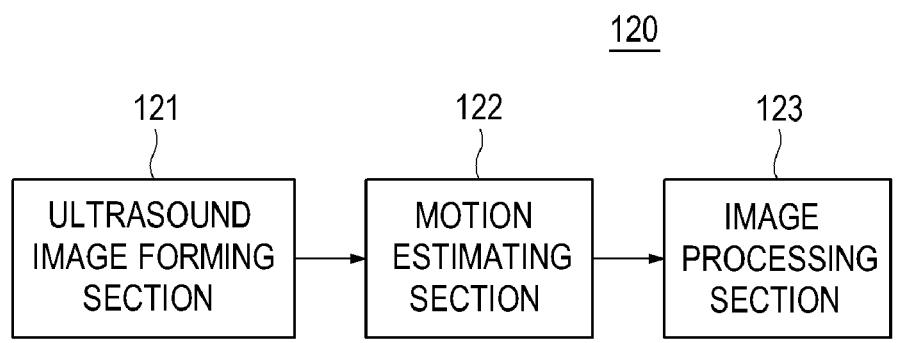
FIG. 3 is a block diagram showing an illustrative embodiment of a processing unit.

FIG. 3 is a block diagram showing an illustrative embodiment of the processing unit 120. The processing unit 120 may include an ultrasound image forming section 121, a motion estimating section 122 and a correcting section 123.

The image forming section 121 may be configured to form the ultrasound images based on the ultrasound data, which may be provided from the ultrasound data acquisition unit 110. The image forming section 121 may repeatedly form the ultrasound images based on the plurality of ultrasound data, which may be provided from the ultrasound data acquisition unit 110, in a sequential manner. The ultrasound images may be sequentially stored in the storage unit 160.

The motion estimating section 122 may be configured to estimate a motion degree of the ultrasound probe 112. In one embodiment, the motion estimating section 122 may be configured to compare an initially formed ultrasound image ("first ultrasound image") with an $N^{th}$ ultrasound image to thereby estimate a motion degree of the ultrasound probe 112, wherein N is a positive integer equal to or greater than 2.

Figure 4:
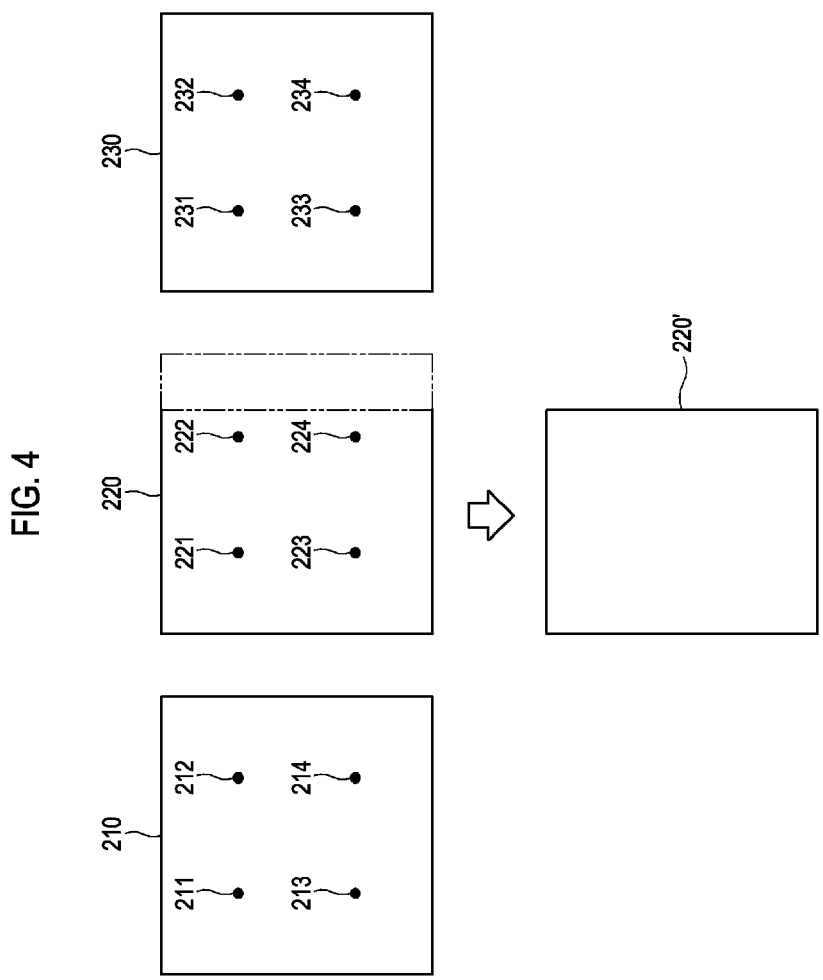
FIG. 4 is a schematic diagram showing an example of processing an ultrasound image according to a motion degree of an ultrasound probe.

In one embodiment, the motion estimating section 122 may be configured to select a plurality of first feature points 211-214 in a first ultrasound image 210, as shown in FIG. 4, and define the first feature points 211-214 as reference feature points. The feature points may be selected by using pixel values of pixels consisting of the ultrasound images. For example, the motion estimating section 122 may be configured to segment the first ultrasound image into a plurality of blocks and select a pixel having a highest pixel value in each of the blocks. The selected pixel may be determined as the feature point in each of the blocks.

The motion estimating section 122 may be further configured to extract a plurality of second feature points 221-224 from a second ultrasound image 220, as shown in FIG. 4. A region indicated by chain lines in FIG. 4 may represent a non-overlapped region with the first ultrasound image. The motion estimating section 122 may be further configured to perform motion tracking between the first feature points 211-214 and the second feature points 221-224 to thereby estimate the motion degree of the ultrasound probe 112 ("first motion degree"). In one embodiment, the motion tracking may be performed by using an evaluation matrix including mean squared error (MME), sum of absolute differences (SAD), mean absolute difference (MAD), sum of square errors (SSE) and sum of absolute transformed difference (SATD), or direct methods including block matching algorithm, phase correlation and frequency domain methods, pixel recursive algorithm and optical flow. The motion estimating section 122 may be further configured to extract a plurality of third feature points 231-234 from a third ultrasound image 230, as shown in FIG. 4. The motion estimating section 122 may perform motion tracking between the first feature points 211-214 and the third feature points 231-234 to thereby estimate a motion degree ("second motion degree").

In another embodiment, the motion estimating section 122 may be configured to detect a plurality of contour points from a first ultrasound image and define a first contour of the target object in the first ultrasound image based on the detected contour points. The motion estimating section 122 may define the first contour as a reference contour. The contour points may be detected by using well-known methods. The motion estimating section 122 may be further configured to detect a plurality of contour points from an $N^{th}$ ultrasound image and define an $N^{th}$ contour of the target object in the $N^{th}$ ultrasound image based on the detected contour points. The motion estimating section 122 may perform the motion tracking between the first contour and the $N^{th}$ contour to thereby estimate a motion degree of the ultrasound probe 112.

In yet another embodiment, the motion estimating section 122 may be configured to define a first contour of the target object on the first ultrasound image based on input information provided from the user input unit 140. The input information may include information for defining a contour of the target object on the ultrasound image. In one embodiment, the user input unit 140 may include a control panel, a mouse, a keyboard and the like. The motion estimating section 122 may be further configured to define an $N^{th}$ contour of the target object on the $N^{th}$ ultrasound image based on input information. The motion estimating section 122 may be configured to perform motion tracking between the first contour and the $N^{th}$ contour to thereby estimate a motion degree of the ultrasound probe 112.

In still yet another embodiment, the motion estimating section 122 may receive a sensing signal from the sensing unit 150 to estimate a motion degree of the ultrasound probe 112 between the first ultrasound image and an $N^{th}$ ultrasound image. The motion estimating section 122 may define a sensing signal, which may be initially provided from the sensing unit 150, as a reference sensing signal. The motion estimating section 122 may be configured to compare the reference sensing signal with a sensing signal, which may be newly provided from the sensing unit 150, to thereby estimate a motion degree of the ultrasound probe 112.

The image processing section 123, which is coupled to the motion estimating section 122, may be configured to perform image processing upon the plurality of ultrasound images based on the estimated motion degree. The image-processed ultrasound images may be stored in the storage unit 160.

In one embodiment, the image processing section 123 may be configured to analyze the first motion degree between the first ultrasound image 210 and the second ultrasound image 220, which are shown in FIG. 4, to determine whether or not the first motion degree is 0. If the motion degree is not 0, i.e., it is determined that the ultrasound probe 112 is moved from an initial position, then the image processing section 123 may be configured to determine similarity between the first ultrasound image 210 and the second ultrasound image 220. The image processing section 123 may be configured to extract a portion 220' of the second ultrasound image 220, which is similar to the first ultrasound image 210, based on the determined similarity. The image processing section 123 analyze the second motion degree between the first ultrasound image 210 and the third ultrasound image 230, which are shown in FIG. 4, to determine whether or not the second motion degree is 0. If the motion degree is 0, i.e., it is determined that the ultrasound probe 112 is not moved from an initial position, then the image processing section 123 may not perform the image processing upon the third ultrasound image 230.

In one embodiment, the image processing section 123 may be further configured to perform filtering (e.g., average filtering, etc.) upon the ultrasound images, which have been sequentially stored in the storage unit 160, i.e., the ultrasound images with the motion corrected. Thus, enhanced ultrasound images may be provided.

In one embodiment, it has been described that the ultrasound image similar to the first ultrasound image is only extracted by using the estimated motion degree. In another embodiment, when the motion of the ultrasound probe occurs, data corresponding to non-overlapped regions between a first ultrasound image and an $N^{th}$ ultrasound image may be obtained through interpolation further to the ultrasound image similar to the first ultrasound image.

The display unit 130 may display the ultrasound images and the image-processed ultrasound images, which may be formed in the processing unit 120. The display unit 140 may include at least one of a cathode ray tube (CRT) display, a liquid crystal display (LCD), an organic light emitting diode (OLED) display and the like.

The sensing unit 150 may be mounted on a predetermined location of the ultrasound probe 112. The sensing unit 150 may be configured to sense a position of the ultrasound probe 112, e.g., 3-dimensional position to thereby output a sensing signal. Any type of devices capable of sensing the position of the ultrasound probe 112 may be used as the sensing unit 150. For example, the sensing unit 150 may include a photo interrupter, a hole sensor, a magnetic sensor, an encoder and the like.

Although embodiments have been described with reference to a number of illustrative embodiments thereof, it should be understood that numerous other modifications and embodiments can be devised by those skilled in the art that will fall within the scope of the principles of this disclosure. More particularly, numerous variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. An ultrasound system, comprising:
an ultrasound acquisition unit including an ultrasound probe for transmitting ultrasound signals to a target object and receiving echo signals, the ultrasound acquisition unit being configured to form a plurality of ultrasound data based on the echo signals; and
a processing unit coupled to the ultrasound acquisition unit and configured to form first to $N^{th}$ ultrasound images by using the plurality of ultrasound data, wherein N is a positive integer greater than 1, the processing unit being further configured to estimate a motion degree of the ultrasound probe and process the $N^{th}$ ultrasound image to correct the $N^{th}$ ultrasound image based on the motion degree, wherein the processing unit includes:
an ultrasound image forming section configured to form the first to $N^{th}$ ultrasound images based on the plurality of ultrasound data;
a motion estimating section configured to estimate a motion degree of the ultrasound probe based on a result of comparing the initially formed first ultrasound image with the $N^{th}$ ultrasound image; and
an image processing section configured to extract a portion similar to the first ultrasound image from the $N^{th}$ ultrasound image based on the motion degree and process the $N^{th}$ ultrasound image based on the extracted portion.

2. The ultrasound system of claim 1, wherein the motion estimating section is configured to extract a plurality of first feature points from the first ultrasound image and a plurality of second feature points from the $N^{th}$ ultrasound image, and perform motion tracking by using the first and second feature points to estimate the motion degree.

3. The ultrasound system of claim 1, wherein the motion estimating section is configured to detect a plurality of contour points from the first ultrasound image and define a first contour of the target object in the first ultrasound image based on the detected contour points, detect a plurality of contour points from the $N^{th}$ ultrasound image and define an $N^{th}$ contour of the target object in the $N^{th}$ ultrasound image based on the detected contour points, and perform the motion tracking between the first contour and the $N^{th}$ contour to estimate the motion degree.

4. The ultrasound system of claim 1, wherein the motion estimating section is configured to define a first contour of the target object on the first ultrasound image based on user input information, define an $N^{th}$ contour of the target object on the $N^{th}$ ultrasound image based on user input information, and perform motion tracking between the first contour and the $N^{th}$ contour to estimate the motion degree.

5. The ultrasound system of claim 1, wherein the image processing unit is configured to analyze the motion degree to determine whether or not the motion degree is 0, and determine, when the motion degree is not 0, differences between the first ultrasound image and the $N^{th}$ ultrasound image, the image processing unit being further configured to extract a portion from the $N^{th}$ ultrasound image that contains no or few differences from a portion of the first ultrasound image.

6. The ultrasound system of claim 1, further comprising a sensing unit mounted on a predetermined position of an ultrasound probe and configured to sense a position of the ultrasound probe to thereby output a sensing signal.

7. The ultrasound system of claim 1, wherein the image processing unit is configured to analyze the motion degree to determine whether or not the motion degree is 0, determine, when the motion degree is not 0, similarity between the first ultrasound image and the $N^{th}$ ultrasound image, extract a portion similar to the first ultrasound image from the $N^{th}$ ultrasound image.

8. The ultrasound system of claim 1, further comprising a storage unit configured to store the ultrasound images sequentially.

9. The ultrasound system of claim 8, wherein the processing unit is configured to perform filtering upon the ultrasound images stored in the storage unit.

10. A method of estimating a motion degree of an ultrasound probe to process an ultrasound image in an ultrasound system, comprising:
   a) transmitting ultrasound signals to a target object and receiving echo signals to form a plurality of ultrasound data based on the echo signals;
   b) forming first to $N^{th}$ ultrasound images by using the plurality of ultrasound data, wherein N is a positive integer greater than 1;
   c) estimating a motion degree of the ultrasound probe by using the ultrasound images;
   d) extracting a portion similar to the first ultrasound image from the $N^{th}$ ultrasound image based on the motion degree; and
   e) processing the $N^{th}$ ultrasound image based on the extracted portion,
   wherein the step c) includes estimating the motion degree of the ultrasound probe based on a result of comparing the initially formed first ultrasound image with the $N^{th}$ ultrasound image.

11. The method of claim 10, wherein the step c) includes:
   extracting a plurality of first feature points from the first ultrasound image;
   extracting a plurality of second feature points from the $N^{th}$ ultrasound image; and
   performing motion tracking by using the first and second feature points to estimate the motion degree.

12. The method of claim 10, wherein the step c) includes:
   detecting a plurality of contour points from the first ultrasound image;
   defining a first contour of the target object in the first ultrasound image based on the detected contour points,
   detecting a plurality of contour points from the $N^{th}$ ultrasound image;
   defining an $N^{th}$ contour of the target object in the $N^{th}$ ultrasound image based on the detected contour points; and
   performing the motion tracking between the first contour and the $N^{th}$ contour to estimate the motion degree.

13. The method of claim 10, wherein the step c) includes:
   defining a first contour of the target object on the first ultrasound image based on user input information;
   defining an $N^{th}$ contour of the target object on the $N^{th}$ ultrasound image based on user input information;
   performing motion tracking between the first contour and the $N^{th}$ contour to estimate the motion degree.

14. The method of claim 10, wherein the step c) includes:
   analyzing the motion degree to determine whether or not the motion degree is 0;
   determining, when the motion degree is not 0, differences between the first ultrasound image and the $N^{th}$ ultrasound image; and
   extracting a portion from the $N^{th}$ ultrasound image that contains no or few differences from a portion of the first ultrasound image.

15. The method of claim 10, further comprising:
   e) storing the image-processed ultrasound images; and
   f) performing filtering upon the stored ultrasound images.

* * * * *